United States Patent [19]

Wiest et al.

[11] Patent Number: 4,874,362

[45] Date of Patent: Oct. 17, 1989

[54] METHOD AND DEVICE FOR INSUFFLATING GAS

[76] Inventors: Peter P. Wiest, Hessenallee 8, 1000 Berlin 19; Hubert Fuchs, Grunewaldstr. 13, 1000 Berlin 41, both of Fed. Rep. of Germany

[21] Appl. No.: 32,005

[22] Filed: Mar. 27, 1987

[30] Foreign Application Priority Data

Mar. 27, 1986 [DE] Fed. Rep. of Germany ....... 3611018

[51] Int. Cl.$^4$ ............................................. A61M 13/00
[52] U.S. Cl. .................................. 604/26; 128/747; 128/748
[58] Field of Search ............... 128/747, 748, 204.19, 128/204.21, 204.23, 204.26, 202.13, 202.16, 205.24; 604/23, 27, 30, 28, 31, 48, 49, 51, 65, 93, 118, 26

[56] References Cited

U.S. PATENT DOCUMENTS

| | | | |
|---|---|---|---|
| 3,383,484 | 5/1968 | Arp et al. | 128/204.23 |
| 3,768,468 | 10/1973 | Cox | 128/204.21 |
| 3,867,941 | 2/1975 | Lindenmann | 128/303 R |
| 3,870,072 | 3/1975 | Lindemann | 604/26 |
| 4,063,548 | 12/1977 | Klatt et al. | 128/748 |
| 4,084,612 | 4/1978 | Baeher | 604/118 |
| 4,207,887 | 6/1980 | Hittebrandt et al. | 128/204.23 |
| 4,215,681 | 8/1980 | Zalkin et al. | 128/204.21 |
| 4,393,869 | 7/1983 | Boyarsky et al. | 128/204.21 |
| 4,441,357 | 4/1984 | Kahn et al. | 128/748 |
| 4,464,169 | 8/1984 | Semm | 604/26 |
| 4,576,035 | 3/1986 | Hooven et al. | 128/748 |
| 4,650,462 | 3/1987 | De Satnick et al. | 604/30 |
| 4,676,774 | 6/1987 | Semm et al. | 128/747 |
| 4,747,403 | 5/1988 | Gluck et al. | 128/204.21 |

FOREIGN PATENT DOCUMENTS

| | | |
|---|---|---|
| 1933768 | 9/1977 | Fed. Rep. of Germany ......... 128/205.24 |
| 3416291 | 3/1985 | Fed. Rep. of Germany ......... 128/204.23 |
| 2026326 | 2/1980 | United Kingdom ........... 128/204.23 |
| 2079984 | 1/1982 | United Kingdom ........... 128/204.21 |

OTHER PUBLICATIONS

"Digital Electronic Control of Automatic Ventilators" by Frank A. Engelman, Jr. et al., IEEE Trans. on Biomed. Eng. 3/77, vol.-24, No. 2, pp. 188-190.
"Computer Control of Respirator and Anaesthesia" by Coles et al.; Med. & Biol. Eng., May 1973, pp. 262-267.
"A Comprehensive Volume Cycled Lung Ventilator Embodying Feedback Control" by Cox et al.; Med. & Biol. Eng.; vol. 12, No. 2, 3/74, pp. 160-169.

Primary Examiner—Lee S. Cohen
Assistant Examiner—David Shay
Attorney, Agent, or Firm—McGlew & Tuttle

[57] ABSTRACT

The invention relates to a method and device for insufflating gas, in particular $CO_2$ into the human or animal body, especially for laparoscope, with an insufflation instrument, for example, a Veress inflow needle, with the following structures arranged successively along a gas line a: pressure reducer $1a$ throughflow meter and pressure meter and with a control circuit connected with the throughflow meter and a pressure meter via respective control lines. The device is without noise-generating magnetic valves, and the intra-abdominal pressure can be measured continuously without elaborate switch overs. The pressure reducer is electrically controllable and connected with the evaluating and control circuit via a control line and is controllable via control line as a function of a clock generator and a nominal pressure generator. In this device, the apparatus pressure is varied, whereby the nominal pressure is reached more rapidly and sudden gas losses can be accommodated better, while a pure filling process can be carried out continuously as well as an actual pressure measurement and also a test cycle.

5 Claims, 6 Drawing Sheets

METHOD AND DEVICE FOR INSUFFLATING GAS

BACKGROUND OF THE INVENTION

FIELD OF THE INVENTION

This invention relates in general to the insufflating of gas to a human or animal body and in particular to a new and useful method device for controlling the flow of insufflating gas.

In a device previously known from German Pat. No. 34 13 631 of this kind, two fixedly preset pressure reducers are provided, which give the gas pressure, for example, preset to 50 mmHg. A succeeding throughflow regulator controls the stream in the gas line, for example, to 1 l/min. The gas flow through a magnetic valve into a throughflow meter, with the pressure drop occurring here as a consequence of frictional resistance being kept constant by the throughflow regualator. The pressure decrease serves at the same time for throughflow reguzltion in the throughflow regulator. Subsequently, the gas streams through an optic throughflow indicating device, before streaming into the insufflation instrument. Immediately in front of it, the pressure meter is connected to the gas line. The known device comprises further, in addition to the main gas line, a branch line, which connects the though flow regualtor with the optic throughflow indicator via a magnetic valve. Both magnetic valves, the pressuremeter unit and the throughflow meter are connected to an electronic evaluating and control circuit, which is provided with an indicating device for total pressure, the intra-abdominal static pressure, the gas flow velocity and the total consumed gas quantity.

The known device, because of the large number of structural elements is elaborate and expensive to produce. Moreover, the two throughflow meters respectively throughflow regulators and the optic throughflow indicator are located in the gas line, by which interferences are created, in particular considerable resistances in the gas stream. Lastly, the process to be carried out with this device of measuring pressure and regulating flow is very complicated. First, on switching on the device, the stream resistance of the entire line system has to be determined, the resistance pressure has to be subtracted from the currently measured pressure at the measuring unit for the determination of the intra-abdominal static pressure. The difference of the two pressure valves gives the ultra-abdominal static pressure. Moreover, at reaching a preseelected nominal pressure, the gas flow is stopped automatically by the electronic control circuit, in the process of which the main gas line leading through the throughflow meter is closed and the branch line opened synchronously. The pressure value at the throughflow regulator is retained. On reaching the preset nominal pressure, the current measured throughflow value is stored in the electronic control circuit and used for determining the intra-abdominal pressure according to a formula in which several measuring parameters are substituted. This determination of the intra-abdominal pressure over flow size and back up pressure at the device output is most uncertain at small pressures and great flow. This, however, is exactly the most common situation in the normal application of this device.

SUMMARY OF THE INVENTION

The invention provides a device for insufflating gas without noise-generating magnetic valves and with the least number possible of components placed in the gas line, the device permitting, without elaborate and complicated switch overs, precision in the measurement of intra-abdominal pressure and in the control of flow.

By comparison to the known device, cost-effective and safety advantages exist in the precise direct measuring of the intra-abdominal pressure without elaborate switching and noise-generating magnetic valves. An essential advantage of the device according to the invention is the continuous automated insufflation, for which the system pressure is varied unlike in the devices known until now, the gas supply is not turned off. In this way, the intra-abdominal nominal pressure is reached more rapidly and a sudden gas loss is accommodated better.

As a function of the preselected nominal pressure and the electric signal of the throughflow meter, the electrically controllable pressure reducer is controlled via the electronic control circuit. The pressure reducer receives its admission pressure from a pressure container or from an additional pressure reducer placed upstream with an exit pressure higher than 50 mmHg, with the control range of the electrically controllable pressure reducer, lying between 0 and 50 mmHg. After switching on the device, the controllable pressure reducer is brought with the electronic control circuit to the preset nominal pressure. If the flow signal detected at the throughflow meter exceeds a value preset in the control circuit, the electronic control circuit regulates the exit pressure of the pressure reducer to the maximum value of 50 mmHg. At the end of a clock period given by the clock generator, the exit pressure of the pressure reducer, controlled by the electronic control circuit is again brought down to the nominal value. The flow signal received by the throughflow meter is evaluated with respect to whether or not the flow at the nominal pressure still exceeds the preset value. If the flow at the preset value exceeds the nominal pressure, the electronic control circuit brings the electrically controllable pressure reducer again for one clock period up to the exit pressure of 50 mmHg. If the flow at the nominal pressure does not exceed the preset value, the electronic control circuit continues to drive the electrically controllable pressure reducer only on the nominal value and monitors the signal of the throughflow meters with respect to whether or not this exceeds the preset value. If this value is exceeded occasionally, the controllable pressure reducer is again brought up to an exit pressure of 50 mmHg for one clock period. The resulting intra-abdominal pressure is measured with the pressure meter when the controllable pressure reducer's exit pressure is down so far that the flow measured with the throughflow meter has just reached zero. The intra-abdominal pressure at this point is equal to the controlled pressure. This is indicated visually. The flow, too, is indicated visually as well as acoustically. The measuring clock rate of the clock generator is independent of the control frequency of the device. For simultaneous self testing, the pressure measured by the pressure meter in the electronic control device is compared to the pressure value indicated at zero flow.

Accordingly, it is the object of the invention to provide an approved device for insufflating gas, particularly carbon dioxide into a human or animal body especially for laparoscopy using an inflow needle which includes a gas line which has a pressure reducer, a throughflow meter a pressure meter which is connected to a control circuit by control lines connected to the throughflow meter and the pressure meter which measures continuously the intra-abdominal pressure wherein the pressure reducer is electrically controllably connected with an evaluating control circuit the control being carried out as a function of a clock generator and a nominal pressure generator wherein the apparatus pressure is varied and the nominal pressure is reached more rapidly and sudden gas losses can be accommodated better than the known devices.

The further object of the invention is to provide a method of controlling the flow of insufflating gas for the subsequent admission into a human or animal body which includes directing the gas through a controllable pressure reducer after the reducer is brought to a pre-set nominal pressure while the gas is directed also through a flow meter and means of depicting its pressure and determining whether it exceeds the pre-set value and thereafter regulating the reducer to have an output of pre-determined maximum value while timing the measurement for a period of time and regulating the reducing valve to return the pressure to a nominal value if it is exceeded.

Further object of the invention is providing a device for insufflating gas, which is simple in design work, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiment of the invention is illustrated.

GENERAL DESCRIPTION OF THE PREFERRED EMBODIMENT

Figure 1:
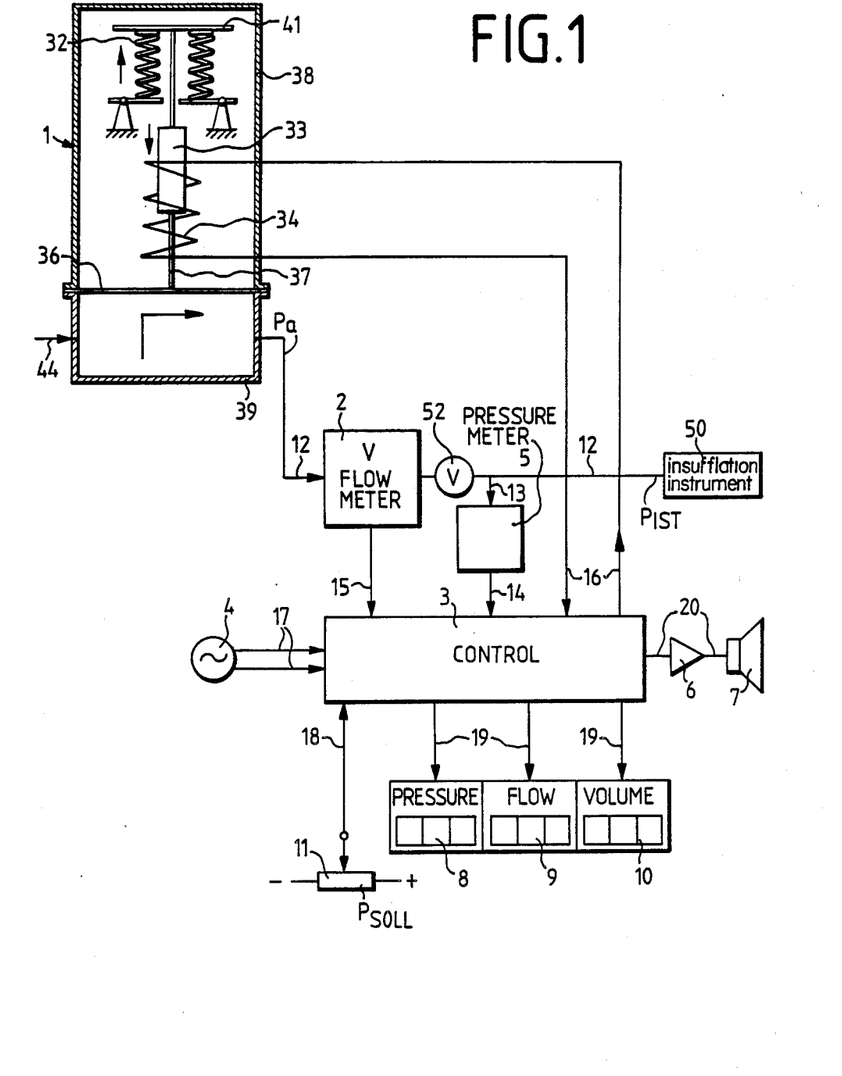
FIG. 1 is a circuit diagram of the entire device for insufflating gas constructed in accordance with the invention.

Referring to the drawings in particular the device for insufflating gas, in particular $CO^2$, into the human or animal body, especially for the purpose of laparoscopy, with an insufflation instrument 50 in particular a Veress inflow needle, comprises the following units arranged successively along a gas line 12: a controllable pressure reducer 1, a throughflow, a volumetric rate of flow meter 2 and a pressure meter 5 set into a branch of the gas line 13. Between the throughflow meter 2, which, particularly, works on the basis of pressure differential, and the branch gas line 13 leading the pressure meter 5, an excess-pressure valve 5a is advantageously included. Further structrual elements in the gas line 12 are not provided, so that it shows the least flow resistances.

Figure 2:
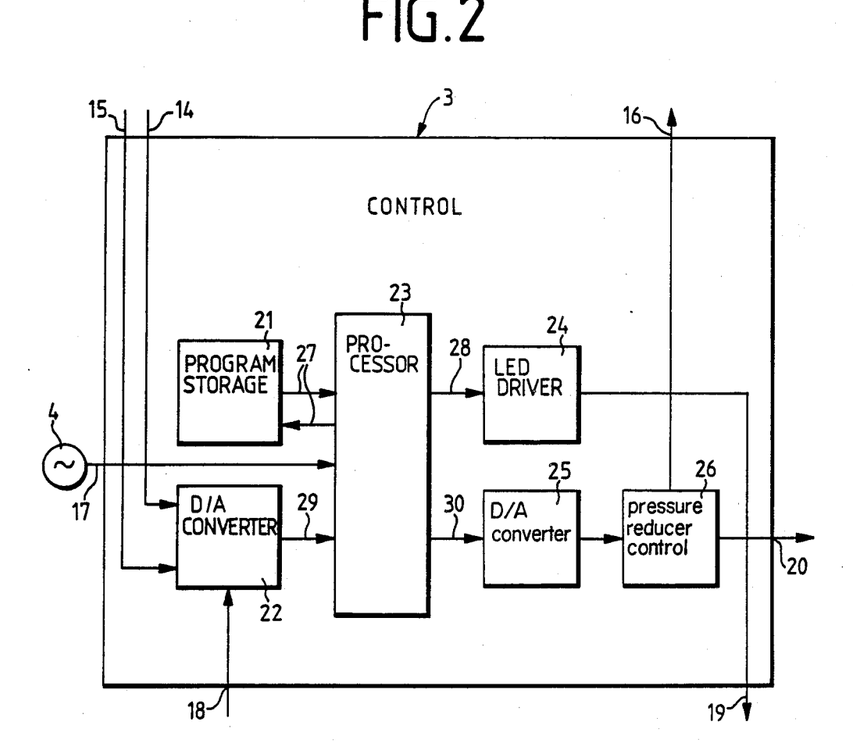
FIG. 2 is an electronic control circuit of the device shown in FIG. 1.
Figure 3:
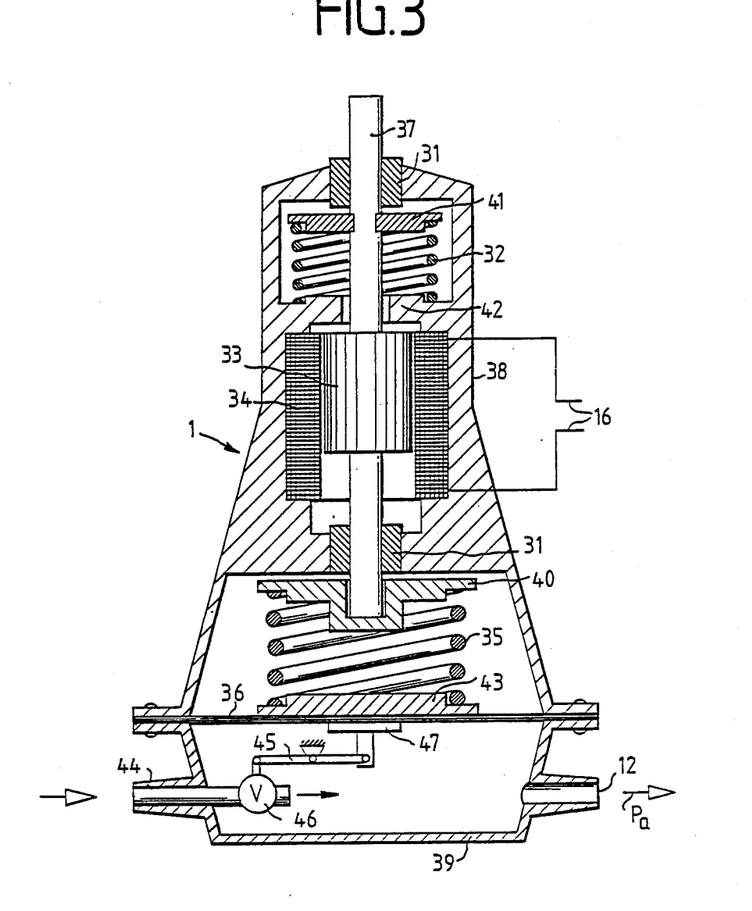
FIG. 3 is an axial sectional view through the electrically controllable pressure reducer of FIG. 1.

An electronic evaluating and control or control circuit 3 is shown in greater detail in a block diagram in FIG. 2. The control circuit 3 has a central processor circuit (CPU) 23, on the inputside of which a program storage 21 is connected, via the control line 17 to a timing clock or timed pulse generator 4 and a 3-channel A-D converter 22 over a control line 29. The converter 22 is connected to the throughflow meter 2 via the control line 15 and to the pressure meter 5 via the control line 14 as well as with a nominal pressure generator 11 via the control line 18. On the output side, to the electronic evaluating and control circuit or processor 23 via a control line 28, and LED driver 24 for indicating pressure, flow and volume at the LED indicators 8, 9 and 10 are connected via the control line 19 and via the control line 30 a 2-channel D-A converter 25 with connected end phase 26, which serves for controlling the electrically controllable pressure reducer 1 via the control lines 16 and for outputting signals via the loud speaker 7 connected via the control line 20. The constructional design of the electrically controllable pressure reducer is shown in FIG. 3. Within the two-part upper and lower housing parts, 38, 39, a control diaphragm is placed, the underside of which actuates a control valve 46 set into the gas line 12 via a two-armed lever 45 mounted centrally on the housing part 39. The lever 45 acts with one end upon a diaphragm plate 47 and with its other upon a control part of the control valve 46 not shown here in detail. The lower housing part 39 is fed on the input side via a gas line 4 from a pressure container—not shown—via an additional pressure reducer possibly connected in series with exit pressure higher than 50 mmHg. The control range of the electrically controllable pressure reducer 1 lies between 0 and 50 mmHg at an exit pressure $P^a$ fed into the gas line 12. In the upper housing part 38, an intake opening facing the control diaphragm 36 is provided for a pressure reducer spring 35, which rests with a spring opposite mounting 43 against the control diaphragm 36. The spring opposite mounting 40 facing away from the control diaphragm 36 is acted upon by the axle 37 of a magnetic core 33, mounted in upper and lower axial friction bearings 31. The magnetic core 33 is surrounded by a magnetic coil 34 mounted in the upper housing part 38. The magnetic coil 34 is electrically connected with the electronic evaluating and control circuit lines 16 via the control circuit 3. The axle 37 is further acted upon over a reset spring 32 extending between a housing bond 42 and a spring counter mounting 41 fixedly mounted on the axle 37. The electrically controllable pressure reducer 1 functions according to the principle pressure gas force equals spring counter force. The resulting path of movement of the control diaphragm 36 opens and closes the control valve 46. The electromagnet formed of the magnetic core 33 and the magnetic coil 34 positions the pressure reducer spring 35 above its spring counter mounting 40. As a result of this, the force of the pressure reducer spring 35 acting upon the control diaphragm 36 changes.

Figure 4A:
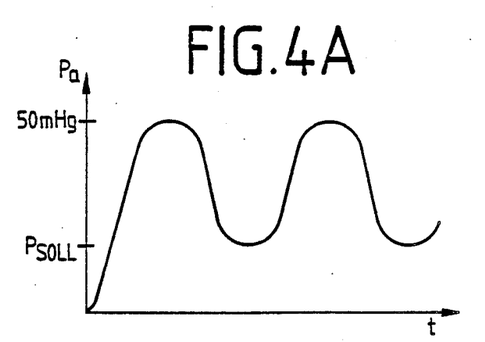
FIGS. 4A, 4B and 4C are curves of the exit pressure $P_a$ of the pressure reducer over time in different stats of operation.
Figure 4B:
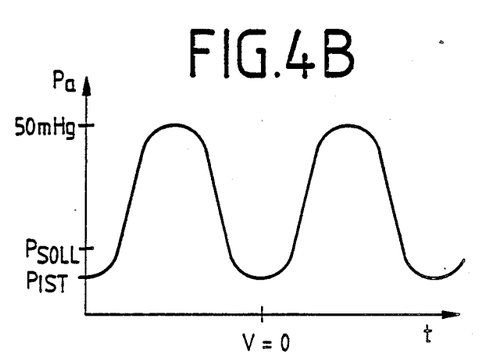

According to FIG. 4A, the exit pressure $P_a$ of the controllable pressure reducer 1 is brought to the nominal pressure $P_{SOLL}$ set with the nominal pressure generator 11 after the device is switched on. If the flow signal detected by the throughflow meter 2 exceeds a value preset in the control circuit, the control electronics 3 regulates the exit pressure of the controllable pressure reducer 1 to the maximum exit pressure $P^a = 50$ mmHg. At the end of a clock period or period given by the timing clock generator 4, the control circuit 3 regulates the pressure $P^a$ again down to the nominal value $P_{SOLL}$. The flow signal is evaluated again by the throughflow meter 2. It is evaluated, whether the flow on reaching nominal pressure $P_{SOLL}$ further exceeds the preset value. If the preset value is exceeded, the control electronics 3 brings the controllable pressure reducer 1 again to the maximum exit pressure of 50 mmHg for one clock period given by the clock generator. If the flow at nominal pressure $P_{SOLL}$ does not exceed the preset value (FIG. 4B), the control electronics 3 regulates the controllable pressure reducer 1 continuously only to the nominal value and monitors the signal of the throughflow meter 2, whether or not it exceeds the preset value. If this value is occasionally exceeded, the controllable pressure reducer 1 is brought up for an additional clock period of the clock generator 4 to $P_a=50$ mmHg. The resulting intra-abdominal pressure is measured with the pressure meter 5 when the controllable pressure reducer 1 has been brought down so far that the flow measured with the throughflow meter 2 has just reached zero as is indicated in FIG. 4B with the value V equal to zero. Then the intra-abdominal pressure $P_{IST}$ is equal the pressure indicated optically on the indicator element. The flow is indicated on the indicator element 9 as well as output acoustically through the loud speakers 7. The measuring clock frequency of the device is independent of the regulating frequency. For simultaneous self-test of the device, the pressure measured with pressure meter 5 in the control electronics 3 is compared with the pressure value, which correspond to the value of the pressure measured with the throughflow meter 2 at zero flow.

The device has thus three different operational states at continuous flow |

1. A pure filling process

This proceeds, as previously described, according to FIG. 4A, with the throughflowmeter 2 continuously taking the values for pressure, flow and volume from the control circuit 3 and indicating them.

2. Actual pressure measurement

This takes place by bringing the controllable pressure reducer 1 down to zero flow according to FIG. 4b. The pressure indicated at the pressure meter 5 then corresponds to the actual intra-abdominal pressure, that is, to pressure $P_{IST}$. That is done only for measurement, not, however, for regulating the insufflation.

3. Test cycle

Figure 4C:
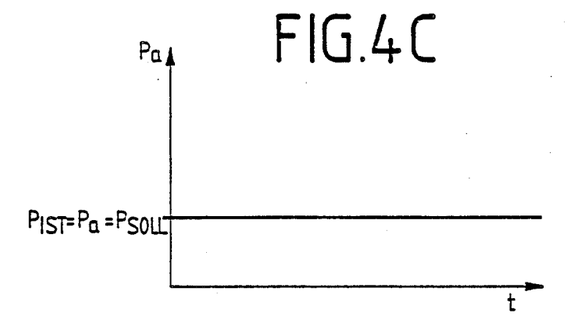

As soon as the exit pressure $P_a$ of the pressure reducer 1 has been brought down to the value of the pressure $P_{IST}$, the control electronics 3 can compare the pressure obtained by the pressure meter 5 and the measured value with the apparatus pressure; in this way, a self-test of the measured pressure takes place (FIG. 4C).

Figure 5:
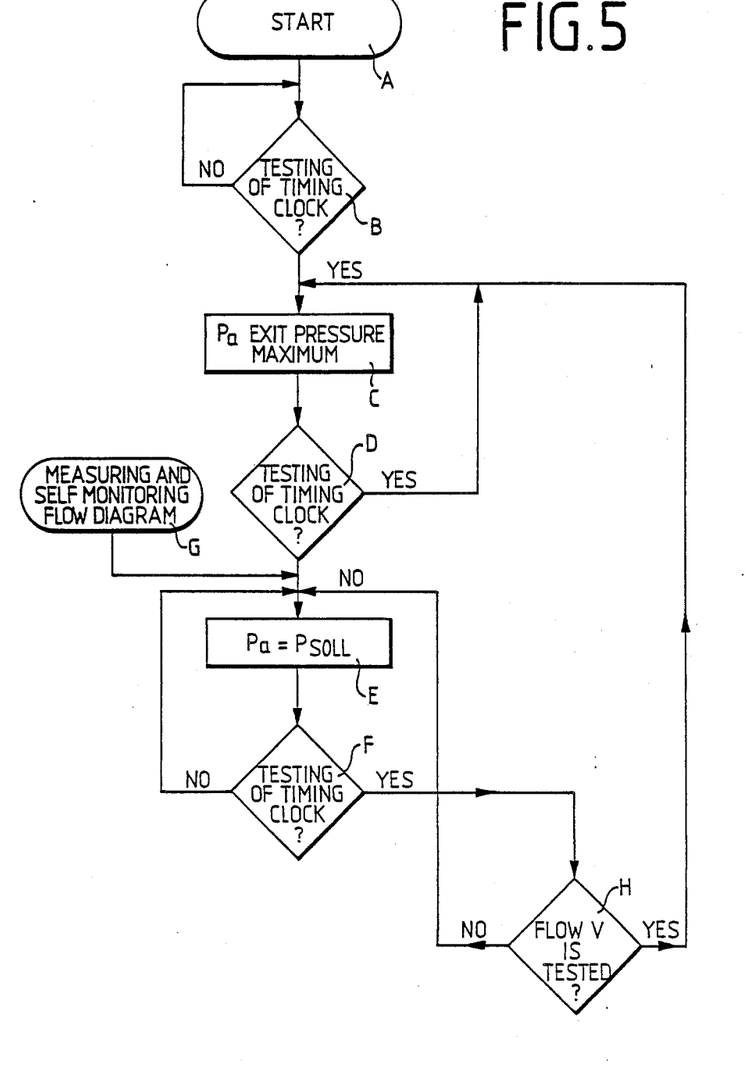
FIG. 5 represents one control cycle-flow diagram and FIG. 6 shows a measuring and self-test flow diagram.
Figure 6:
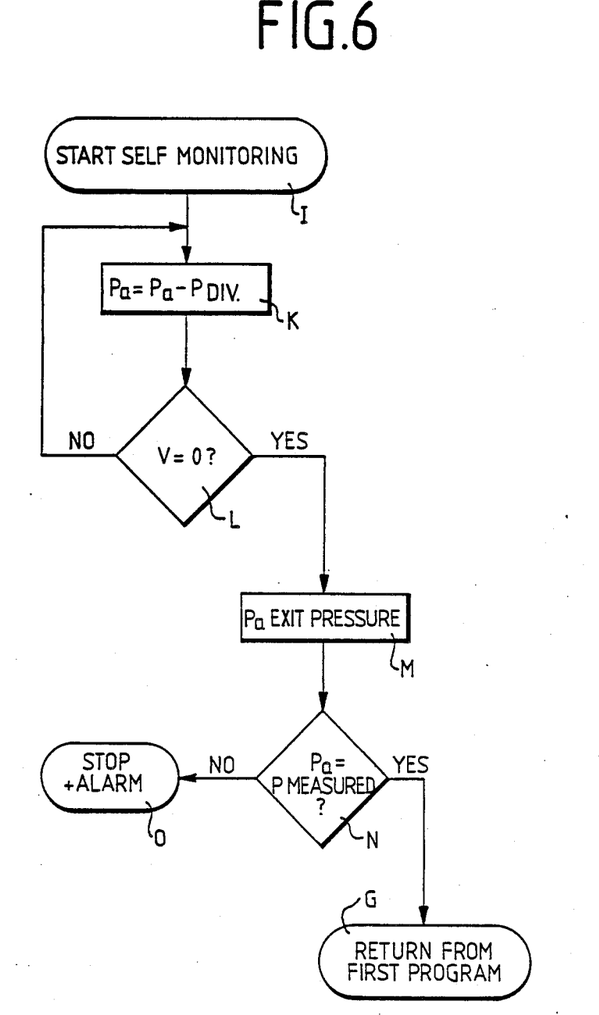

In FIGS. 5 and 6, regulating and measuring and self-monitoring flow diagrams are shown. Block A "Start" means switching on the device. In block B, the clock of the timing clock generator 4 is tested. In block C, the exit pressure $P_a$ of the electrically controllable pressure reducer 1 is set to the maximum exit pressure $P_a$ equal to 50 mmHg. In block D, the clock of the clock generator 4 is tested again. In block E, the exit pressure $P_a$ of the settable pressure reducer 1 is adjusted to the nominal pressure $P_{SOLL}$ set on the nominal value generator 11. In block F, the clock of the clock generator 4 is again tested. In block H, the flow V is tested. If it is greater than the smallest flow $V_{MIN}$ when the actual pressure $P_{IST}$ is a little smaller than the nominal pressure $P_{SOLL}$ then resetting to block C takes place. If V is smaller than $V_{min}$, resetting to block E takes place. The pressure $P_{IST}$ is the actual pressure in the abdomen, i.e. the intra-abdominal pressure. Block G refers to the measuring and self-monitoring flow diagram according to FIG. 6.

Initiating self-monitoring takes place in block I. In block K, the exit pressure $P_a$ of the controllable pressure reducer 1 is reduced by a pressure difference $P_{DIV}$ of approximately 2 mmHg. In block L, determination takes places whether flow V has reached zero flow. If yes, the exit pressure $P_a$ of the controllable pressure reducer 1 is indicated in block M. In block N is determined, whether the indicated exit pressure $P_a$ corresponds to pressure P measured, measured with the pressure meter 5. If this is not the case, then block 0 follows, according to which the device is stopped and an alarm is triggered. If the exit pressure $P_a$ at the controllable pressure reducer 1 corresponds to pressure P measured, measured with the pressure meter 5, block G is executed, i.e. a return to the main program according to the regulating cycle flow diagram in accordance with FIG. 5 takes place.

Presetting the value for the nominal flow takes place in the program storage 21 of the control circuit 3.

While a specific embodiment of the invention has been shown and described in detail to illustrate the application of the principles of the invention, it will be understood that the invention may be embodied otherwise without departing from such principles.

What is claimed is:

1. A device for controlling the admission of insufflating gas in to a body cavity through an inflow needle, particularly for laparoscopy comprising:

a pressure gas line;

a pressure reducer means connected to said gas line for supplying gas at a pressure reducer exit pressure, which is a working pressure to the needle;

a pressure meter connected to said gas line downstream of said pressure reducer means and means for outputting a signal representative of gas pressure in said gas line;

a flow meter connected to said gas line downstream of said pressure reducer means and means for outputting a signal representative of gas flow in said gas line;

a clock pulse generator means for providing a timed pulse;

a nominal pressure generator means for maintainning a preset nominal pressure; and, control means operatively connected to said pressure reducer means via a pressure a reducer means control line, connected to said pressure meter via a pressure meter line for receiving a signal representative of gas pressure in said gas line, connected to said flow meter via a flow meter line for receiving a signal representative of gas flow in said gas line, connected to said pulse generator means for receiving a continuous timed pulse signal and connected to said nominal pressure generator means via a pressure generator means control line, said control means being for varying the working pressure as a function of said timed pulse signal by repeatedly, at successive clock pulses, controlling said pressure reducer means to reach a preset nominal gas line pressure in said pressure gas line in response to a signal from said nominal pressure generator means and for repeatedly operating said flow meter to detect the gas flow rate through said flow line, comparing at successive clock pulses, the gas flow rate detected by the flow meter at the preset nominal gas pressure to a preset flow rate value and regulating the pressure reducer exit pressure to a maximum pressure value of 50 mm Hg, higher than the nominal pressure set by the nominal pressure generator means and back to the preset nominal gas pressure for subsequent comparisons if the flow meter indicates a flow rate exceeding the preset flow rate value until the flow rate falls to the preset value, and regulating the pressure reducer means to an exit pressure equal to the preset nominal pressure value, if the flow measured by said flow meter at said preset nominal gas pressure is less than the preset flow rate value.

2. A device for controlling the filling of insufflating gas according to claim 1, wherein said pressure reducer means includes a housing connected in said gas line; a control diaphragm means in said housing for varying the volume of said housing; a control valve means in said gas line for regulating the flow of said gas into said housing; a pressure reducer spring acting on one side of said control diaphragm means to urge said control diaphragm means into said housing for reducing the volume of said housing; an axle including an end portion connected to said pressure reducer spring; and, magnetic control means connected to said pressure reducer control line, said magnetic control means for acting on said axle to move said axle to vary the action of said spring on said diaphragm means.

3. A device according to claim 1 including means for subsequently controlling the pressure reducer means so that the pressure in said gas line is at the preset nominal exit pressure until the flow rate is zero.

4. A method for controlling the flow of insufflating gas through a flow line to a needle for inflating a body cavity, particularly for laparoscopy, comprising the steps of:
   directing gas in the flow line, under pressure, through a controllable pressure reducer to reach a preset nominal gas line pressure;
   detecting the gas flow rate through the flow line at the preset nominal gas pressure;
   repeatedly comparing at successice clock intervals the detected gas flow rate at the preset nominal gas pressure with a preset flow rate value and regulating the pressure reducer exit pressure to a maximum value of 50 mm Hg, higher than the preset nominal gas pressure, and back to the preset nominal gas pressure value for subsequent comparisons if the flow rate exceeds the preset flow rate value until the flow rate falls to said preset flow rate value; and, regulating the pressure reducer exit pressure to said preset nominal gas pressure if the flow at said preset nominal gas pressure is less than said preset flow rate value.

5. A method according to claim 4 including the step of measuring the body cavity pressure when the gas flow rate is zero.

* * * * *